United States Patent [19]

Maleski

[11] Patent Number: 5,250,741
[45] Date of Patent: Oct. 5, 1993

[54] PROCESS FOR THE PREPARATION OF 5-ALKOXY-2-NITROSO PHENOLS

[75] Inventor: Robert J. Maleski, Kingsport, Tenn.

[73] Assignee: Eastman Kodak Company, Rochester, N.Y.

[21] Appl. No.: 912,372

[22] Filed: Jul. 13, 1992

[51] Int. Cl.$^5$ .................. C07C 41/18; C07C 201/00; C07C 315/04; C07C 67/313
[52] U.S. Cl. .................. 568/587; 568/586; 568/30; 558/389; 560/61
[58] Field of Search .............. 568/587, 586, 30; 558/389; 560/61

[56] References Cited

U.S. PATENT DOCUMENTS 3,683,034  9/1972  Doering et al. .............. 568/587
3,933,926  1/1976  Salter et al. ................. 260/622
4,242,277 12/1980  Tanaka et al. ............... 260/396

OTHER PUBLICATIONS

J. D. Richey et al., *Agr. Biol. Chem.*, 39, 683 (1979).
E. H. Allen et al., *J. Org. Chem.*, 36, 2004 (1971).
J. Jahelka et al., *Collection Czechoslov. Chem. Commun.*, 38, 877 (1973).
H. H. Hodgson et al., *J. Chem. Soc.*, 2775 (1929).

*Primary Examiner*—Marianne M. Cintins
*Assistant Examiner*—Margaret J. Page
*Attorney, Agent, or Firm*—J. Frederick Thomsen; William P. Heath, Jr.

[57] ABSTRACT

Disclosed is a process for the preparation of 5-alkoxy-2-nitrosophenols by the nitrosation of 3-alkoxyphenols using an alkali metal nitrite and an alkanoic acid wherein the selectivity of the nitrosation is improved. Also disclosed is a 2-step process for the preparation of 5-alkoxy-2-nitrophenols by oxidizing the 5-alkoxy-2-nitrosophenols obtained in accordance with the present invention.

3 Claims, No Drawings

PROCESS FOR THE PREPARATION OF 5-ALKOXY-2-NITROSO PHENOLS

This invention pertains to the preparation of 5-alkoxy-2-nitrosophenols by the nitrosation of 3-alkoxyphenols using an alkali metal nitrite and an alkanoic acid wherein the selectivity of the nitrosation is improved. This invention also pertains to the preparation of 5-alkoxy2-nitrophenols by oxidizing the 5-alkoxy2-nitrosophenols obtained in accordance with the present invention.

5-Alkoxy-2-nitroso (and 2-nitro) phenols are valuable intermediates useful in the synthesis of a variety of industrial and agricultural chemicals. For example, 5-methoxy-2-nitrosophenol and 5-methoxy-2 nitrophenol are used in the synthesis of 6-methoxy-2(3H)-benzoxazolinone, an important pesticide [Allen et al, J. Org. Chem., 36, 2004 (1971) and German Offen. 2,131,366].

The preparation of 5-alkoxy-2-nitrosophenols is known. For example, according to Hodgson et al, J. Chem. Soc., 2775 (1929), 3-alkoxyphenols (resorcinol monoalkyl ethers) may be nitrosated by the addition of sufficient sulfuric acid to an aqueous solution of sodium nitrite, sodium hydroxide and the 3-alkoxyphenol to make the resulting solution strongly acidic. This method provides good yields but the product is contaminated with resinous product of over-oxidation and about 30 weight percent of the isomeric 3-alkoxy-4-nitrosophenol. Such contamination requires extensive purification procedures to obtain the 5-alkoxy-2-nitrosophenol in sufficient purity for further use. Alternatively, Henrich et al, Chem. Ber., 35, 1475 (1902) disclose that an aqueous solution of sodium nitrite may be added to a 3-alkoxyphenol dissolved in acetic acid and alcohol. The product thus obtained is contaminated with the same impurities described hereinabove.

Similar problems with positional isomers are present in the direct nitration of 3-alkoxyphenols and over oxidation problems are much more severe. Thus, the addition of nitric acid to a solution of a 3-alkoxyphenol dissolved in acetic acid produces such an impure product that addition of water to the reaction solution produces a tar from which pure nitro compound can be isolated only in poor (26%) yields by steam distillation, an expensive and laborious technique. See Richey et al, Agr. Biol. Chem., 39, 683 (1979).

It is known [Houben Weil Method der Organische Chemie, X/1, 864 (1971)] that certain aromatic nitroso compounds are readily oxidized by a variety of oxidizing agents. Since preliminary introduction of the nitroso group occurs under conditions milder than those needed for the direct introduction of the nitro group, nitrosation followed by oxidation of the thus formed nitroso compound is the preferred method for synthesis of some aromatic nitro compounds. However, nitrosation of 3-alkoxyphenols results in the formation of a gross mixture of products from which the desired nitro compound can be obtained in low yield by means of difficult purification procedures.

I have now discovered that 5-alkoxy-2-nitrosophenols can be prepared in improved purity and yields by performing the nitrosation in the presence of a liquid reaction medium comprising at least about 70 weight percent of an aliphatic carboxylic acid having up to about 5 carbon atoms. The present invention therefore provides a process for the preparation of a 5-alkoxy-2-nitrosophenol which comprises contacting an aqueous solution of an alkali nitrite with a solution of a 3-alkoxyphenol in an aliphatic, carboxylic acid having up to about 5 carbon atoms at a temperature of about $-10°$ to 25° C., wherein the liquid reaction medium of the resulting mixture comprises at least about 70 weight percent of the aliphatic carboxylic acid. My novel process provides alkoxy-nitrosophenols which consist of at least 90 mole percent, preferably at least 95 mole percent, of the 3-alkoxy-2-nitrosophenol isomer.

The alkoxy group of the 3-alkoxyphenols may be straight- or branched-chain, unsubstituted or substituted alkoxy having up to about 12 carbon atoms. Examples of substituents which may be present on the alkoxy groups include alkoxy, aryloxy, halogen, nitro, alkylsulfonyl, arylsulfonyl, cyano and alkoxycarbonyl. The alkoxy group of the 3-alkoxyphenol reactants preferably is unsubstituted alkoxy of up to about 6 carbon atoms with methoxy being especially preferred.

Although, as specified hereinabove, the carboxylic acid employed as the reaction medium may contain up to about 5 carbon atoms, the carboxylic acid preferably is selected from acetic acid, propionic acid and mixtures thereof. The amount of carboxylic acid(s) employed may be varied considerably provided that the amount used is sufficient to dissolve most or all of the 3-alkoxyphenol reactant. Typically, the amount of carboxylic acid(s) reaction medium used will give a carboxylic acid(s) to 3-alkoxyphenol reactant weight ratio of about 5:1 to 15:1.

The nitrosation process of the present invention may be carried out at a temperature in the range of about $-10°$ to 25° C., preferably about $-10°$ to 10° C. and most preferably about $-5°$ to 0° C. It will be apparent to those skilled in the art that utilizing temperatures in the preferred range will preclude the use of acetic acid as the sole carboxylic acid reaction medium. Thus, the process preferably is carried out at a temperature of about $-10°$ to 10° C. using a carboxylic acid reaction medium comprising propionic acid or a mixture of acetic and propionic acid, e.g., mixtures in which the weight ratio of acetic to propionic acids is about 1:1 to 2.5:.

The alkali metal nitrite preferably is either sodium or potassium nitrite. The amount of alkali metal nitrite used normally is at least one mol of nitrite per mol of 3-alkoxyphenol reactant with a maximum of 1.2 mols of alkali metal nitrite per mol 3-alkoxyphenol reactant. In the practice of the nitrosation process, the alkali metal nitrite is added as an aqueous solution to a solution of the 3-alkoxyphenol in the carboxylic acid(s). The amount of water present in the alkali metal nitrite aqueous solution preferably is about 1.5 to 2 parts by weight per part by weight of alkali metal nitrite, i.e., water:nitrite weight ratios of about 1.5:1 to 2:.

As specified hereinabove, the nitrosation process is performed in the presence of a liquid reaction medium comprising at least about 70 weight percent of an aliphatic carboxylic acid having up to about 5 carbon atoms. The remaining 30 weight percent of the reaction medium may be comprised of water from the nitrite solution and minor amounts of other materials such as up to about 5 weight percent of alkanol. The reaction medium liquid preferably comprises at least 85 weight percent of one or more carboxylic acids.

The reaction mixture resulting from the addition of the aqueous solution of alkali nitrite to the solution of 3-alkoxyphenol in the aliphatic, carboxylic acid normally is agitated for a period of time, e.g., from about 0.5 to 3 hours, sufficient to complete the reaction as determined by thin layer chromatography. The 5-alkoxy-2-nitrosophenol product is substantially insoluble in the liquid reaction medium and thus can be isolated by conventional solid/liquid separation procedures.

The nitrosation process described hereinabove may be used advantageously in combination with known oxidation process wherein an oxidizing agent such as nitric acid, hydrogen peroxide, a percarboxylic acid, e.g., peracetic acid, and the like is added to the product slurry obtained from the nitrosation process to convert the 5-alkoxy-2-nitrosophenol to the corresponding 5-alkoxy-2-nitrosophenol. The present invention therefore includes a process for the preparation of 5-alkoxy-2-nitrosophenols by the steps comprising:

(1) contacting an aqueous solution of an alkali nitrite with a solution of a 3-alkoxyphenol in an aliphatic, carboxylic acid having up to about 5 carbon atoms at a temperature of about −10° to 25° C., wherein the liquid reaction medium of the resulting mixture comprises at least about 70 weight percent of the aliphatic carboxylic acid to produce a slurry of a 5-alkoxy-2-nitrosophenol; and (2) adding to the slurry produced in step (1) a sufficient quantity of an oxidizing agent to convert the 5-alkoxy-2-nitrosophenol to the 5-alkoxy-2-nitrophenol.

The impurities produced by the nitrosation step remain dissolved in the carboxylic acid reaction medium during the oxidation step. Thus, the 5-alkoxy-2-nitrophenol product of good to excellent purity may be obtained by separating the solid product from the final reaction mixture.

The temperature at which the oxidation step is performed is similar to that described above for the nitrosation step except that temperatures above about 10° C. normally should be avoided. Useful oxidizing agents are those known to oxidize aromatic nitroso compounds to the corresponding nitro compounds. Examples of suitable oxidizing agents include nitric acid, hydrogen peroxide, and percarboxylic acids such as peracetic acid. The concentration of the hydrogen peroxide and nitric acid employed is not critical since the addition of significant quantities of water in the second (oxidation) step is not detrimental to the oxidation process. The concentration of the nitric acid may be from 70 to 98 weight percent whereas the concentration of the hydrogen peroxide may be from 3to 90 weight percent, preferably 30 to 70 weight percent. Nitric acid is the preferred oxidizing agent. The amount of the oxidizing agent employed typically is about 1.5 to 3equivalents of oxidizing agent per mol of 5-alkoxy-2-nitrosophenol compound.

The processes of the present invention are further illustrated by the following examples. The composition of each product was determined by NMR and is given as a weight percent.

EXAMPLE 1

A solution of sodium nitrite (6.9 g, 0.1 mol) dissolved in 15 mL water was added, dropwise, to a solution of 3-methoxyphenol (12.4 g, 0.1 mol) dissolved in propionic acid (100 mL) cooled to −5° to 0° C., at a rate which maintained a temperature of −5° to 0° C. The mixture was stirred for 1 hour to produce a slurry of alkoxy nitrosophenols having a mole ratio of 5-methoxy-2-nitrosophenol to 3-methoxy-4-nitrosophenol of 95:5. Water (85 mL) was added to the slurry and the product was collected by filtration, washed with 60 mL of 50% aqueous propionic acid and then dried to give 10.1 g (66% of theory) of 5-methoxy-2-nitrosophenol which contained approximately 2% of the 3-methoxy-4-nitrosophenol isomer.

EXAMPLE 2

The procedure described in Example 1 was repeated except that no water was added and the product was washed with 60 mL of propionic acid. The yield of 5-alkoxy-2-nitrosophenol (containing approximately 2% of the 3-methoxy-4-nitrosophenol isomer) was 8.6 g (56% of theory).

EXAMPLE 3

Example 2 was repeated except that the propionic acid was replaced with the same amount of acetic acid and the nitrosation was carried out at 20°–25° C. The yield of 5-methoxy-2-nitrosophenol (containing approximately 2% of the 3-methoxy-4-nitrosophenol isomer) was 8.3 g (54% of theory).

EXAMPLE 4

A solution of 3-methoxyphenol (37.2 g, 0.3 mol) in propionic acid (300 mL) was cooled to −5° to 0° C. and a solution of sodium nitrite (21 g, 0.304 mol) in 50 mL water was added dropwise at a rate which maintained the temperature at −5° to 0° C. The resulting mixture was stirred for 1 hour to produce a slurry to which was added dropwise 98% nitric acid (37.9 g, 0.59 mol) while maintaining the temperature in the −5° to 0° C. range. The mixture was stirred 1 hour at −5° to 0° C. and then was stirred an additional 2 hours while the temperature was allowed to rise to 20° C. Water (250 mL) then was added dropwise to the reaction mixture and stirred for 0.5 hour. The product was collected by filtration, washed with 300 mL of 50% aqueous propionic acid and then with a large volume of water, and dried. The yield of 5-methoxy-2-nitrophenol was 29.4 g, 58% of theory. No impurities were detectable by NMR analysis.

The invention has been described in detail with particular reference to preferred embodiments thereof, but it will be understood that variations and modifications can be effected within the spirit and scope of the invention.

I claim:

1. Process for the preparation of a 5-alkoxy-2-nitrosophenol which comprises contacting an aqueous solution of an alkali nitrite with a solution of a 3-alkoxyphenol in an aliphatic, carboxylic acid having up to about 5 carbon atoms at a temperature of about −10° to 25° C., wherein the liquid reaction medium of the resulting mixture comprises at least about 70 weight percent of the aliphatic carboxylic acid and wherein at least one mol of alkali nitrite per mol of 3-alkoxyphenol is used.

2. Process for the preparation of a 5-alkoxy-2-nitrosophenol which comprises contacting an aqueous solution of an alkali nitrite selected from sodium and potassium nitrite with a solution of a 3-alkoxyphenol in a aliphatic, carboxylic acid selected from propionic acid and mixtures of acetic and propionic acids at a temperature of about −10° to 10° C., wherein the liquid reaction medium of the resulting mixture comprises at least about 85 weight percent of the aliphatic carboxylic acid and wherein at least one mol of alkali nitrite per mol of 3-alkoxyphenol is used.

3. Process according to claim 2 wherein the 5-alkoxy-2-nitrosophenol is 5-methoxy-2-nitrosophenol and the 3-alkoxyphenol is 3-methoxyphenol.

* * * * *